US00PP25535P2

(12) United States Plant Patent
Zampini

(10) Patent No.: US PP25,535 P2
(45) Date of Patent: May 12, 2015

(54) ***HYDRANGEA* PLANT NAMED 'FIPRIZAM'**

(50) Latin Name: *Hydrangea macrophylla*
Varietal Denomination: Fiprizam

(71) Applicant: LCN Holdings, Inc., Perry, OH (US)

(72) Inventor: James W. Zampini, Madison, OH (US)

(73) Assignee: Lake Country Nusery, Perry, OH (US)

( * ) Notice: Subject to any disclaimer, the term of this patent is extended or adjusted under 35 U.S.C. 154(b) by 26 days.

(21) Appl. No.: 13/986,358

(22) Filed: Apr. 23, 2013

Related U.S. Application Data

(60) Provisional application No. 61/687,408, filed on Apr. 24, 2012.

(51) Int. Cl.
*A01H 5/00* (2006.01)

(52) U.S. Cl.
USPC ..... Plt./250

(58) Field of Classification Search
USPC ..... Plt./250
See application file for complete search history.

*Primary Examiner* — June Hwu
*Assistant Examiner* — Keith Robinson
(74) *Attorney, Agent, or Firm* — Penny J. Aguirre

(57) ABSTRACT

A new cultivar of *Hydrangea macrophylla* named 'Fiprizam', that is characterized by its foliage that is variegated with creamy white centers and dark green margins, and its leaves with margins that are ruffled, crinkled, and rugose.

1 Drawing Sheet

Botanical classification: *Hydrangea macrophylla.*
Varietal denomination: 'Fiprizam'.

BACKGROUND OF THE INVENTION

The present invention relates to a new and distinct cultivar of *Hydrangea macrophylla* and will be referred to hereafter by its cultivar name, 'Fiprizam'. 'Fiprizam' represents a new lace cap type *Hydrangea*, a deciduous shrub grown for landscape use and for use as a potted plant.

'Fiprizam' was discovered by the Inventor as a naturally occurring branch mutation of 'Maresii' (not patented) that was growing in a container in a nursery in Perry, Ohio in 2009.

Asexual reproduction of the new cultivar was first accomplished by the Inventor using softwood stem cuttings in Perry Ohio in 2009. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Fiprizam' as a unique cultivar of *Hydrangea macrophylla.*

1. 'Fiprizam' exhibits foliage that is variegated with creamy white centers and dark green margins.
2. 'Fiprizam' exhibits leaves with margins that are ruffled, crinkled, and rugose.

'Maresii', the parent plant of 'Fiprizam', differs from 'Fiprizam' in having foliage that is non-variegated. 'Fiprizam' can be most closely compared to the cultivars 'Maresii Varegata' (not patented) and 'Variegata' (not patented). 'Maresii Varegata' differs from 'Fiprizam' in having variegated foliage that is comprised of green foliage with variable thin stripes of white. 'Variegata' differs from 'Fiprizam' in having variegated foliage comprised of green centers and white margins.

BRIEF DESCRIPTION OF THE DRAWINGS

The accompanying colored photograph illustrate the overall appearance and distinct characteristics of the new *Hydrangea* as grown in a greenhouse in Perry, Ohio. The photograph was taken of a two year-old plant of 'Fiprizam' as grown in a 2-gallon container.

The photograph in FIG. 1 provides a close-up view of the foliage of 'Fiprizam'.

The colors in the photographs may differ slightly from the color values cited in the detailed botanical description, which accurately describe the colors of the new *Hydrangea.*

BOTANICAL DESCRIPTION OF THE PLANT

The following is a detailed description of two year-old plants of 'Fiprizam' as grown in a greenhouse in 2-gallon containers in Perry, Ohio. Phenotypic differences may be observed with variations in environmental, climatic, and cultural conditions. The color determination is in accordance with The 2007 R.H.S. Colour Chart of The Royal Horticultural Society, London, England, except where general color terms of ordinary dictionary significance are used.

General description:

*Plant type.*—Deciduous shrub, lace cap type *Hydrangea.*

*Plant habit.*—Broadly upright, well branched.

*Height and spread.*—Reaches about 1.2 m in height and 1.5 m in width in four years in the landscape.

*Hardiness.*—At least in U.S.D.A. Zones 5 to 9.

*Diseases resistance.*—Has been observed to be tolerant to powdery mildew caused by *Erysiphe polygoni.*

*Root description.*—Fine.

Growth and propagation:

*Propagation.*—Softwood stem cuttings, an average of 10 months from propagation to flowering plant.

*Root development.*—Roots initiate in 2 weeks, roots fully develop in a 2.5 inch container in about 60 days.

*Growth rate and vigor.*—Slow.

Stem description:

*Stem shape.*—Round, solid.

*Stem strength.*—Strong.

*Stem color*.—Young growth; 145B, mature growth; 199C.

*Stem size*.—Main stem an average of 30 cm, average of 4 mm in diameter with lateral branches an average of 12 cm in length and 3 mm in width on a two-year-old plant.

*Stem surface*.—Glabrous and glossy.

*Internode length*.—Average of 6 cm.

*Branching*.—An average of 3 lateral branches on a two year-old plant.

Foliage description:

*Leaf shape*.—Elliptic.

*Leaf arrangement*.—Opposite.

*Leaf division*.—Simple.

*Leaf number*.—Average of 4 pairs per lateral branch.

*Leaf base*.—Cuneate.

*Leaf apex*.—Acuminate.

*Leaf margins*.—Serrated, ruffled, crinkled, rugose.

*Leaf venation*.—Pinnate, color 145B in centers and 137B in margins on upper and lower surface.

*Leaf size*.—An average of 13 cm in length and 6 cm in width.

*Leaf attachment*.—Petiolate.

*Leaf surface*.—Smooth and glabrous in centers, semi-glossy and rugose on margins on upper and lower surface.

*Leaf color*.—Young foliage upper surface; centers 155C, margins a blend of N137 and 137A, young foliage lower surface; centers 155C, margins a blend of N137 and 137A, mature foliage upper surface; centers 155C, margins a blend of N137 and 137A, mature foliage lower surface; centers 155C, margins a blend of N137 and 137A.

*Petioles*.—Average of 2 cm in length and 2 mm in diameter, 145B in color, glabrous surface.

Inflorescence description: Flowers have not developed on plants available for data collection to date. The new cultivar is grown for its unique foliage.

It is claimed:

1. A new and distinct cultivar of *Hydrangea* plant named 'Fiprizam' substantially as herein illustrated and described.

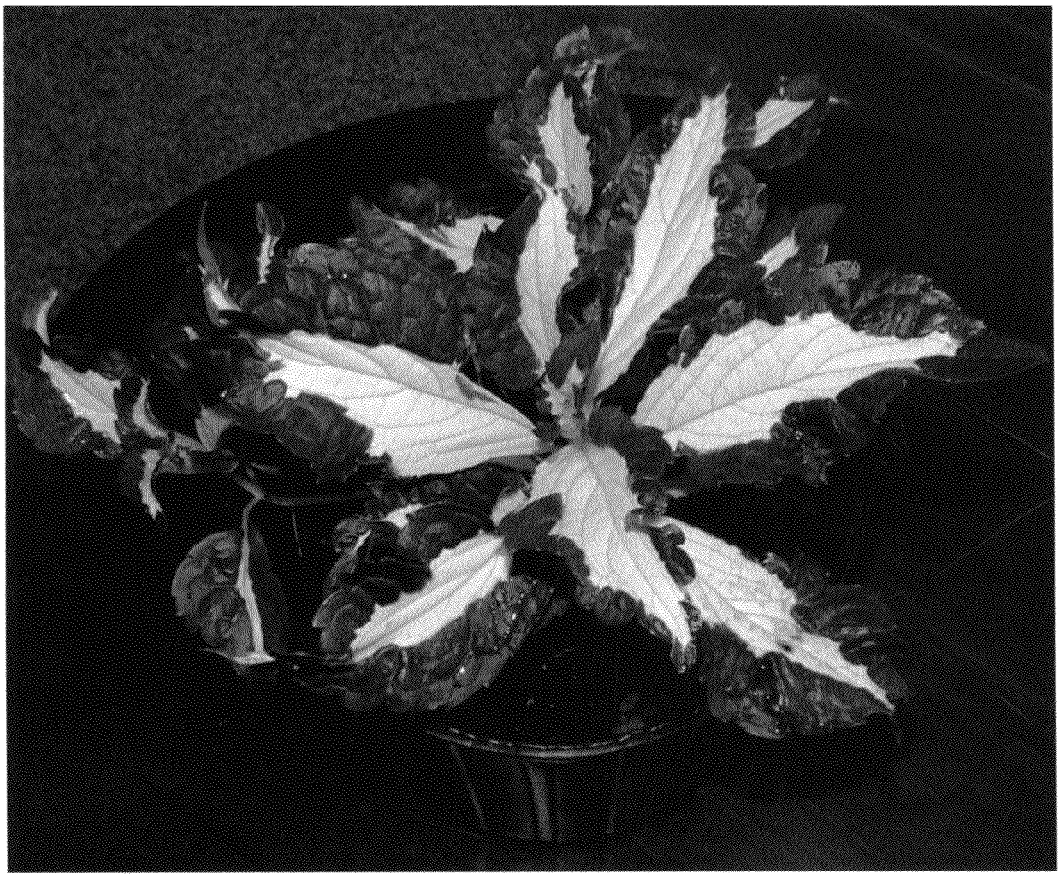

* * * * *